US008366758B2

(12) United States Patent
Ahlering et al.

(10) Patent No.: US 8,366,758 B2
(45) Date of Patent: Feb. 5, 2013

(54) HYPOTHERMIA FOR IMPROVING RATE OF FUNCTIONAL RECOVERY FOLLOWING PELVIC SURGERIES

(75) Inventors: Thomas E. Ahlering, Laguna Niguel, CA (US); David S. Finley, Long Beach, CA (US)

(73) Assignee: The Regents of the University of California, Oakland, CA (US)

( * ) Notice: Subject to any disclaimer, the term of this patent is extended or adjusted under 35 U.S.C. 154(b) by 168 days.

(21) Appl. No.: 12/867,247

(22) PCT Filed: Feb. 11, 2009

(86) PCT No.: PCT/US2009/033820
§ 371 (c)(1),
(2), (4) Date: Aug. 11, 2010

(87) PCT Pub. No.: WO2009/102803
PCT Pub. Date: Aug. 20, 2009

(65) Prior Publication Data
US 2010/0324545 A1    Dec. 23, 2010

Related U.S. Application Data (60) Provisional application No. 61/065,483, filed on Feb. 11, 2008, provisional application No. 61/081,365, filed on Jul. 16, 2008.

(51) Int. Cl.
*A61F 7/00* (2006.01)
*A61F 7/12* (2006.01)
(52) U.S. Cl. ...................................... 607/105
(58) Field of Classification Search ............ 607/105
See application file for complete search history.

(56) References Cited

U.S. PATENT DOCUMENTS

| 6,009,351 | A | 12/1999 | Flachman |
| 6,641,602 | B2 * | 11/2003 | Balding .......... 607/105 |
| 6,726,708 | B2 * | 4/2004 | Lasheras ........ 607/105 |
| 2002/0151943 | A1 | 10/2002 | Balding |
| 2003/0028180 | A1 | 2/2003 | Franco |
| 2006/0118127 | A1 | 6/2006 | Chinn |
| 2006/0161107 | A1 * | 7/2006 | Mantle .......... 604/113 |
| 2008/0033471 | A1 | 2/2008 | Paz et al. |
| 2009/0270955 | A1 * | 10/2009 | Magers et al. ...... 607/105 |

OTHER PUBLICATIONS

Thuroff et al, "High-Intensity Focused Ultrasound: Complications and Adverse Events," Molecular Urology, 2000, vol. 4, No. 3, pp. 183-187; p. 184, right column, para 1-2; p. 186, Table 2; p. 186-187. "Conclusion" Section.

* cited by examiner

*Primary Examiner* — Roy Gibson
*Assistant Examiner* — Kaitlyn Smith
(74) *Attorney, Agent, or Firm* — VENABLE LLP; Stefan J. Kirchanski (57) ABSTRACT

Hypothermia significantly improves the rate of recovery of function following abdominal surgery—particularly radical prostatectomy. Prior to commencing surgery the tissues at and surrounding the site of the surgery are cooled by means of an endorectal cooling balloon inserted into the patient's rectum. The uninflated balloon is inserted and then inflated with cooling fluid which fluid is constantly circulated in and out to lower the temperature. Improved hypothermia can be achieved by bathing internal tissue with chilled water or buffer. Limitation of surgically induced damage can be demonstrated by the more rapid regain of continence in radical prostatectomy patients treated with hypothermia during surgery.

18 Claims, 4 Drawing Sheets

HYPOTHERMIA FOR IMPROVING RATE OF FUNCTIONAL RECOVERY FOLLOWING PELVIC SURGERIES

CROSS-REFERENCE TO PRIOR APPLICATIONS

The present application is a U.S. National Phase application of and claims priority from PCT/US2009/033820, filed on Feb. 11, 2009 designating the United States, which in turn was based on and claims priority from U.S. Provisional Patent Application Nos. 61/065,483 filed Feb. 11, 2008 and 61/081,365 filed Jul. 16, 2008 all of which applications are incorporated herein by reference.

U.S. GOVERNMENT SUPPORT

Not Applicable

BACKGROUND OF THE INVENTION

1. Area of the Art

The present invention is in the area of medical devices and procedures and is more specifically directed towards a medical device and procedure for limiting nerve and inflammatory damage during pelvic surgeries, particularly during radical prostatectomy.

2. Background

Many surgical procedures have at least some side effects. Not unexpectedly, the more extensive the surgery, the more extensive the likely side effects. However, even relatively limited surgeries may have temporary or permanent side effects. In particular pelvic surgeries such as those dealing with the urogenital system may have more or less pronounced side effects. For example, the relatively common radical prostatectomy may have a variety of side effects. Following prostate surgery the patient often experiences temporary or even prolonged-permanent difficulties with urinary incontinence. In addition, prostate surgery frequently results in minor to profound sexual dysfunction. This is, perhaps, not surprising because male sexual functioning relies on an interaction between the nervous system, the endocrine system and the circulatory system. The pelvic region is a plexus of many nerves, and nerve fibers may be severed or damaged during prostate surgery. Furthermore, removal of the prostate traumatizes neuromuscular tissues causing inflammation and subsequent dysfunction. As a result, increasingly sophisticated and relatively non-invasive prostate surgeries have been developed to "spare nerves." Many of these procedures involve microscopic robotic surgeries. With these techniques one can demonstrate that few if any nerves are actually severed. Nevertheless, these surgeries continue to result in significant urinary incontinency and impotence in patients due to stretching of the nerves (traction injury) as well as inflammatory damage resulting in dysfunction of surrounding structures. This problem is not unique to prostatectomy—other pelvic surgeries such as extravesical ureteral reimplantation, radical cystectomy, colorectal surgery including abdominal perineal resection, low anterior resection, and transabdominal or transvaginal gynecologic surgery including radical hysterectomy, total abdominal hysterectomy, laparoscopic or robotic hysterectomy, vaginal hysterectomy, pelvic organ prolapse repair, bladder surgery and sacrocolpopexy can all potentially result in significant side effects (i.e. urinary retention, urinary incontinence) which appear to involve nerve damage (due to secondary inflammatory effects)—even where the surgeries are carefully designed to spare nerves.

During radical prostatectomy dissection of the bladder neck, mobilization of the neurovascular bundles (NVBs), and transection of the urethra and external sphincter complex may all cause acute neuromuscular injury that is largely responsible for delayed recovery of urinary continence and sexual function. The primary injury results from the mechanical trauma of dissection, nerve traction, and the use of thermal energy (cautery) which leads to neurapraxia or axonotmesis of pelvic autonomic nerves and muscle/cellular degeneration and/or other damage. A secondary (indirect) wave of damage often ensues due to inflammation. The inflammatory cascade includes tissue swelling (edema), activation of coagulation factors, pro-inflammatory cytokine formation, hypoxia, acidosis, free radical production, and apoptosis. White blood cell (macrophage and neutrophil) infiltration with subsequent release of reactive oxygen species and hydrolytic enzymes further contributes to secondary tissue damage. Both modes of injury (primary and secondary) can contribute to varying degrees to the post-operative functional deficits in urinary (i.e. intrinsic sphincter deficiency and detrusor dysfunction) and sexual (i.e. nerve conduction block) function.

Although various drug-based approaches exist to treat inflammation, none of them appear to simultaneously treat the multiple modes of inflammation that follow pelvic surgery; nor do any of them appear to be suited for local application. There remains a need to reduce collateral tissue damage and side effects of pelvic surgery and to improve the rate of functional recovery following pelvic surgery.

SUMMARY OF THE INVENTION

The present invention relates to methods and systems for applying local hypothermia during pelvic surgeries for the reduction of collateral tissue damage that may occur during the surgery. The use of local hypothermia in the pelvic region to reduce tissue and inflammatory damage results in improved functional recovery rates following the surgery.

Applicants have demonstrated an improved rate of return to urinary continence following the prostatectomy through application of local hypothermia to the entire pelvic region during surgery. Local hypothermia was achieved through use of an endorectal cooling balloon system which was inflated with cooling liquid to occupy the rectal space after which the cooling liquid was cycled continuously into and out of the inflated balloon to cool the region. Statistical analysis of the surgical outcomes demonstrated a statistically significant correlation between hypothermia during surgery and more rapid return to urinary continence. Incontinence is used as a surrogate for nerve and other tissue damage resulting from the surgery. The results clearly demonstrate that hypothermia during surgery reduce collateral damage. It is expected that hypothermia during abdominal surgery will also speed the recovery of other functions such as sexual potency.

In one aspect of the present invention, methods are provided for improving recovery of a biological function of a patient following surgery of the pelvis comprising inducing local hypothermia in the pelvic region during surgery through use of a cooling balloon catheter positioned in the rectum of the patient. The methods comprise introducing the cooling balloon catheter into the rectum prior to surgery, inflating the cooling balloon catheter so that the cooling balloon catheter engages the rectal wall and fills the rectal lumen, introducing cooling fluid into the cooling balloon catheter thus lowering the temperature of the balloon catheter and tissue in contact with the balloon catheter, and performing the surgery under conditions of hypothermia, thus improving recovery of a biological function of the patient.

In one aspect of the present invention, methods are provided for improving recovery of a biological function of a patient following surgery of the pelvis comprising inducing local hypothermia in the pelvic region during surgery through use of a cooling balloon catheter positioned in the vagina of the patient.

In another aspect of the present invention, systems are provided for improving recovery of a biological function of a patient following surgery of the prostate, the system comprising a cooling balloon catheter for insertion into the rectum of the patient, a means for inflating the cooling balloon catheter so that the cooling balloon catheter engages the rectal wall extending from the membranous urethra to the seminal vesicles, and means for cooling the cooling balloon catheter thereby inducing hypothermia in the prostate and surrounding tissues.

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide methods and devices for inducing hypothermia during pelvic surgery—particularly radical prostatectomy.

It is well established that cooling can reduce the consequences of acute trauma (i.e. traction, ischemia, etc.) and the inflammatory cascade. Cooling profoundly reduces an array of damaging effects such as microcirculatory impairment due to endothelial damage, activation of the coagulation cascade, leukocyte infiltration, free radical production, cytokine formation, acidosis, apoptosis, release of proteolytic enzymes and tissue destruction [Yeh et al. (2004) Cardiovasc. Surg. 128:203-10; Sadgrove et al. (2004) J. Neurochem. 91:327-36; Kawamura et al. (2005) Exp. Neurol. 195:305-12; Westermann et al. (1999) Surgery 126:881-9; Deal et al. (2002) J. Bone Joint Surg Am 84:1573-8; Laing et al. (1973) NZ Med J. 78:155-8; Schaser (2007) Am. J. Sports Med. 35:93-102]. Without being bound by any particular theory, pre-emptive hypothermia may preserve tissues from damage by lowering the tissues' metabolic rates and oxygen demands. Indeed, it has been demonstrated that for each degree the temperature is lowered, a 5% reduction in oxygen consumption is achieved [Yeh et al. (2004) Cardiovasc. Surg. 128:203-10]. As a result of lowered temperature, less lactate formation occurs, protein synthesis and cell signaling are preserved, and most importantly, the inflammatory response is blunted [Sadgrove et al. (2004) J. Neurochem. 91:327-36; Kawamura et al. (2005) Exp. Neurol. 195:305-12]. In addition, cooling should minimize the damaging effects of thermal energy (cautery) applied during surgery, thereby reducing collateral tissue damage.

Applicants applied local hypothermia to the entire pelvic region during surgery for excising the prostate with the goal of reducing collateral damage as evidenced by return to urinary continence and ultimately return to sexual potency. Because return to potency can be relatively slow and contains a significant subjective component, continence is used here as a more readily measured surrogate. Data show that return to continence may potentially be correlated with return to potency. To achieve their goal Applicants designed an endorectal cooling balloon which was used during the surgery in conjunction with adjunctive intracorporeal cold irrigation. As described herein, the cooling was applied during 50 consecutive patients undergoing Robot-assisted Laparoscopic Prostatectomy (hRLP).

Further, these methods and systems are fully applicable to limiting loss of function in a variety of abdominal surgeries. Where a pelvic surgical procedure is carried out on a female, hypothermia is readily achieved by insertion of a cooling balloon into the vagina as well (or instead) of the rectum. The cooling balloon placed in the rectum or vagina effectively cools the regional tissues, e.g., rectum, vagina, pelvic nerves, urethra, bladder, uterus, and prostate, without obstructing the surgical field. Accordingly, in other embodiments, induced local hypothermia of the present invention is used in conjunction with pelvic surgery including, but not limited to, extravesical ureteral reimplantation, radical cystectomy, colorectal surgery such as abdominal perineal resection, low anterior resection, and transabdominal or transvaginal gynecologic surgery such as radical hysterectomy, total abdominal hysterectomy, laparoscopic or robotic hysterectomy, vaginal hysterectomy, pelvic organ prolapse repair, bladder surgery and sacrocolpopexy. Adjunctive intra-corporeal irrigation, for example with 4° C. sterile water, may be used as well in the pelvic surgery, as appropriate, for additional cooling of the regional tissues.

The incidence of urinary incontinence (i.e. the number, if any, urinary pads used to treat incontinence) following radical prostatectomy (RP) in modern series ranges from 5.8%-37.9% [Burkhard et al. (2006) J. Urol. 176:189-95; Touijer et al. (2008) J. Urol. 179:1811-7; Penson et al. (2005) J. Urol. 173:1701-5]. Although most men ultimately regain urinary control, incontinence has a major negative impact on quality of life [Litwin et al. (2001) J. Urol. 166:587-92]. RP associated incontinence is thought to be related to a low urethral closing pressure due to intrinsic sphincteric deficiency (ISD) and to a lesser extent bladder dysfunction [Hammerer et al. (1997) J. Urol. 157:233-6; Ficazzola et al. (1998) J. Urol. 160:1317-20]. Indeed, urodynamically proven ISD was reported in 35%-67% of the cases as the sole contributing factor to incontinence and in 64%-96% of the cases in combination with detrusor instability in one report [Ficazzola et al. (1998) J. Urol. 160:1317-20]. Other factors such as age, AUA symptom score, prostate weight, and erectile dysfunction have been reported to play a role in delay of continence [Rogers et al. (2006) J. Urol. 176:2448-52; Milhoua et al. (2008) Urology 71:417-20; Nandipati et al. (2007) Urology 70:1127-30; Rocco et al. (2006) J. Urol. 175:2201-6; Wei et al. (2000) J. Urol. 164:744-8].

Inflammation of the bladder, urethra and sphincter mechanism secondary to dissection of the bladder and prostate may be contributing factors to transient incontinence. Acute injury and downstream sequelae of inflammation are linked to muscle and nervous tissue damage and dysfunction due to cellular edema, acidosis, nerve conduction blockade, free radical damage and apoptosis [Ni Choileain et al. (2006) Surgery 4:23-31; Osborn (1990) Cell 62:3-6; Weiss (1989) N. Engl. J. Med. 320:365-76]. Accordingly, in one aspect of the present invention, methods and systems are used to provide local hypothermia to the pelvis to pre-emptively attenuate inflammation caused by excision of the prostate, thereby resulting in earlier return to continence and potency. In one embodiment, methods and systems of the present invention result in an improvement in recovery rate of a biological function following pelvic surgery, for example, in return of urinary continence or in return of sexual potency. For example, in one embodiment, the patient returns to urinary continence within one month of surgery. In other embodiments, the patient returns to urinary continence within 2 months of surgery or within 3 months of surgery.

Figure 1:
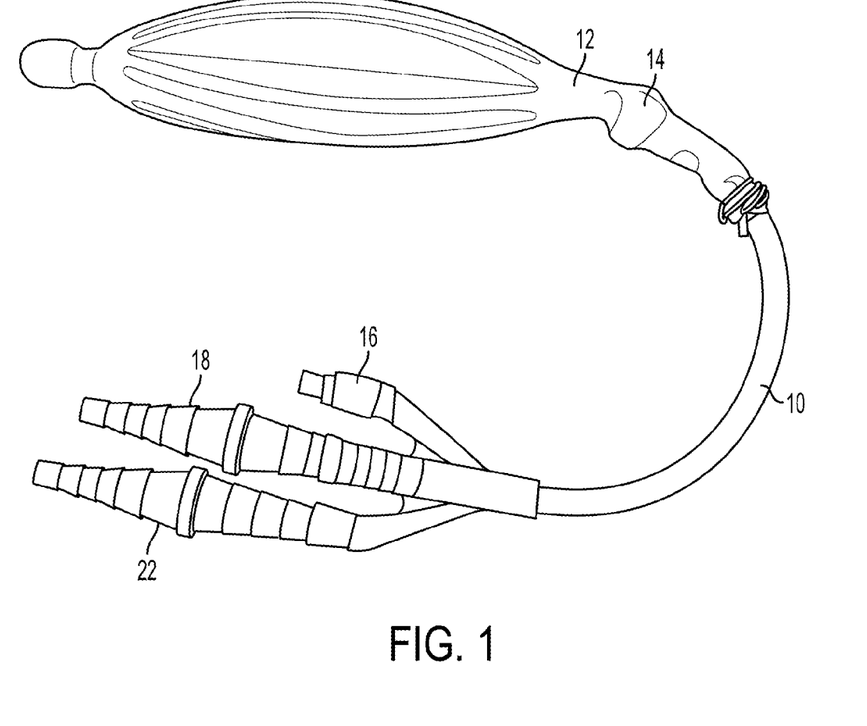
FIG. 1 shows a perspective view of an endorectal cooling balloon.

In one embodiment, local hypothermia is achieved by use of an endorectal cooling balloon system (ECB). The prototype ECB system was based on a 40 cm, 24Fr three-way latex urethral catheter which was placed inside a 5"×2.5" elliptical latex balloon chosen to distend at low pressure and conform to the rectal wall without excessive deformation. As shown in FIG. 1, for example, the end of a urethral catheter 10 was inserted into the latex balloon 12 and tied in place. The outline of the end of the catheter with an uninflated retention balloon 14 can be seen through the latex balloon 12. A port 16 of the catheter 10 connects to the retention balloon 14 and was used to inflate the inner retention balloon 14. Ports 18 and 22 represent the influx and efflux, respectively, of cooling fluid circulating in the outer latex balloon 12. In use the outer balloon 12 was inflated with cooling liquid to occupy the rectal space; then cooling liquid was flowed into and out of the inflated balloon 12 to maintain the desired temperature.

In an exemplary embodiment, anatomically, the ECB is designed to extend from the membranous urethra to the seminal vesicles when in use. For use, the lubricated and uninflated ECB is inserted through and just inside the patient's anus and anchored by inflating the retention balloon 14 to about 20 cc with water. The outer latex balloon is then distended and cycled (using ports 18 and 22) continuously with cold saline (4° C.) delivered via gravity from a source 40 cm above the patient. The ECB volume is approximately 200 cc which volume was selected to fall well below known maximum isobaric rectal distention volumes and diameters of approximately 315 ml and 6.2 cm, respectively [Gladman et al. (2006) Dis. Col. Rectum 50:621-9].

Alternately, the cooling liquid can be delivered by any number of known cooling fluid systems that recirculate cooling fluid from a chilled bath. In such a case the cooling fluid may contain an antifreeze such as glycerin or propylene glycol, and the chilling bath contains either a mechanical or electronic (Peltier effect) refrigeration system that maintains the cooling fluid at a desired temperature. Differential pressure regulators can be used to ensure that the balloon 12 stays fully inflated but does not exert excessive force against the rectal walls. Adjunctive 4° C. sterile water (or sterile physiological buffer) intra-corporeal irrigation may be used to augment cooling of the ECB. The temperature of the ECB cooling fluid and that of the irrigation liquid can be adjusted as desired—particularly where a recirculation system is employed. With use of the methods and systems described herein, intra-corporeal temperature in the pelvic region of the patient may range from 10 to 32° C. In some embodiments, the intra-corporeal temperature may be, for example, in the range of 10-25° C., 15-25° C., 10-20° C., 10-15° C., or 20-30° C. In some embodiments, the intra-corporeal temperature may be less than 10° C.

The endovaginal cooling balloon system of the present invention is similarly configured but of a shape and size appropriate for use in a vagina. The endovaginal cooling balloon is of a material and shape such that, when positioned in the patient, the balloon can distend at low pressure and conform to the vaginal wall without excessive deformation. A catheter is similarly used for circulating the cooling fluid. The endovaginal cooling balloon may be used alone or in conjunction with an ECB.

Different configurations of the ECB can be used to obtain improved temperature control. It is possible to use the inner balloon of the design as the cooling source by exchange cooling fluid therein. In such a case the outer balloon can serve as a temperature buffer with a temperature sensor located in contact with the fluid of the outer balloon. The inner balloon can then be brought to a lower temperature until the fluid within the outer balloon approaches the target temperature at which time the temperature of the inner balloon can be modulated to prevent excessive cooling. Under such conditions it can be assumed the temperature within the outer balloon is essentially equivalent to the surface temperature of the inner rectal tissues. This may be a correct assumption when the volume of the outer balloon exceeds that of the inner balloon only by a relatively small percentage so that the liquid buffer layer between the inner balloon and the outer balloon is thin—say a centimeter or even less.

In the tests reported herein a 9Fr esophageal probe (Smiths Medical ASD, Rockland, Mass.) was used to obtain intracorporeal temperature readings (T) directly along the anterior surface of the rectum/NVB. Alternatively or in addition, temperature readings may be taken at other anatomical points. For example, a temperature sensor (thermocouple or thermistor) can be integrated into a laparoscopic "bulldog" clamp placed on the vascular pedicle of the prostate. It is also possible to place temperature sensors within the ECB or on the surface of the ECB to measure rectal temperatures. In the reported tests intracorporeal temperature readings were captured during two time intervals: Phase 1 and Phase 2. Generally the entire hRLP surgery lasts about 4 hours. In Phase 1, cooling was started 10 minutes before the prostatic vascular pedicle was transected and was discontinued just before the completion of the urethral transection. Hypothermia was discontinued to spatially facilitate the apical dissection and anastomosis. In Phase 2, cooling was reinstituted following the anastomosis and continued until just before the patient was extubated. In some instances, cooling may be continued for a longer period of time (e.g., before and/or after the surgery) to further limit any inflammatory response.

In some cases of pelvic surgery, cooling of the pelvic area may be initiated prior to surgery so that the desired tissue area may be pre-cooled, for example, cooling may be initiated immediately after the patient is intubated, at least about 2-2.5 hours prior to Phase 1, at least about 2.5 hours before surgery, at least about 2 hours before surgery, at least about 1.5 hours before surgery, at least about 1 hour before surgery, or at least about 30 minutes before surgery. In some pelvic surgery cases, cooling of the pelvic area may be continued for up to 2, 3, 4, 5, 6, 7, 8 or 12 hours post-operatively.

EXAMPLE

Surgery with Intra-Operative Cooling

Fifty consecutive men underwent Hypothermic Nerve Sparing Robot-assisted Laparoscopic Prostatectomy (hRLP). Two patients were excluded due to prior failed radiotherapy; one patient was withdrawn due to technical difficulties associated with the ECB. All procedures were performed by a single surgeon (TA). Standard pertinent clinical data such as age, BMI, abbreviated International Index of Erectile Function score (IIEF-5 score), American Urological Association symptom score (AUAss), urinary bother score, prostate weight, PSA level, Gleason score, cT-stage, and nerve sparing was entered prospectively into an electronic database (Table 1). Institutional review board approval and HIPAA compliance were observed. As presented herein, urinary incontinence is used as a surrogate for nerve and other tissue damage resulting from surgery. The results clearly demonstrate that hypothermia during surgery reduce collateral damage.

The normothermic group was stratified into subgroups to control for learning curve and evolution of specific changes in technique: case #1-250, case #251-450, case #451-592, and case #593-667. In addition to being the most recent group of patients, case #593-667 marked the initiation of posterior reconstruction as described by Rocco and colleagues. In the hRLP group (case #668-717) the technique (i.e. the Rocco suture) was not changed; the only change was the addition of the hypothermia.

TABLE 1

Baseline characteristics of the hypothermia and control groups

| | Control Group (#1-665) | | hRLP (#666-718) | | t-test |
|---|---|---|---|---|---|
| | Mean | SD | Mean | SD | p-value |
| Age (years) | 61.3 | 7.4 | 59.9 | 6.9 | 0.200 |
| AUAss | 8.7 | 7.2 | 7.7 | 6.2 | 0.386 |
| IIEF-5 | 19.0 | 7.5 | 22.7 | 2.9 | 0.001 |
| Pre-PSA | 6.7 | 6.2 | 6.0 | 6.4 | 0.463 |
| BMI | 26.9 | 3.4 | 26.5 | 2.8 | 0.524 |
| Prostate weight (g) | 52.0 | 21.2 | 54.4 | 18.6 | 0.463 |
| | Frequency | Percent | Frequency | Percent | Chi-square p-value |
| Stage: | | | | | |
| I | 386 | 65 | 26 | 58 | 0.236 |
| II | 187 | 32 | 17 | 38 | |
| III | 17 | 3 | 2 | 4 | |
| Nerve-sparing: | | | | | |
| None | 34 | 6 | 0 | 0 | 0.549 |
| Unilateral | 159 | 27 | 13 | 28 | |
| Bilateral | 396 | 67 | 34 | 72 | |

Local hypothermia was achieved by use of an endorectal cooling balloon system (ECB). The prototype system was based on a 40 cm, 24Fr three-way latex urethral catheter which was placed inside a 5"×2.5" elliptical latex balloon chosen to distend at low pressure and conform to the rectal wall without excessive deformation. FIG. 1 shows an early version of the ECB. The end of the urethral catheter 10 was inserted into the latex balloon 12 and tied in place. The outline of the end of the catheter with an uninflated retention balloon 14 can be seen through the latex balloon 12. A port 16 of the catheter 10 connects to the retention balloon 14 and was used to inflate the inner retention balloon 14. Ports 18 and 22 represent the influx and efflux, respectively, of cooling fluid circulating in the outer latex balloon 12. In use the outer balloon 12 was inflated with cooling liquid to occupy the rectal space; then cooling liquid was flowed into and out of the inflated balloon 12 to maintain the desired temperature.

Anatomically, the ECB extends from the membranous urethra to the seminal vesicles when in use. The lubricated and uninflated ECB was inserted through and just inside the patient's anus and anchored by inflating the retention balloon 14 to about 20 cc with water. The outer latex balloon was then distended and cycled (using ports 18 and 22) continuously with cold saline (4° C.) delivered via gravity from a source 40 cm above the patient. The ECB volume was approximately 200 cc which volume was selected to fall well below known maximum isobaric rectal distention volumes and diameters of approximately 315 ml and 6.2 cm, respectively [Gladman et al. (2006) Dis. Col. Rectum 50:621-9]. Adjunctive 4° C. sterile water (or sterile physiological buffer) intra-corporeal irrigation was used to augment cooling of the ECB.

A 9Fr esophageal probe (Smiths Medical ASD, Rockland, Mass.) was used to obtain intracorporeal temperature readings (T) directly along the anterior surface of the rectum/NVB. In the tests intracorporeal temperature readings were captured during two time intervals: Phase 1—starting 10 minutes before the prostatic vascular pedicle was transected and discontinued just before the completion of the urethral transection. Hypothermia was discontinued to spatially facilitate the apical dissection and anastomosis. Phase 2—cooling was reinstituted following the anastomosis and continued until just before the patient was extubated. Generally the entire surgery lasted about 4 hours. In the initial procedures the cooling was initiated just prior to Phase 1-approximately two hours after the surgery began. Cooling was started at the beginning of Phase 1 up to case # 690. At case # 690 and beyond the cooling was initiated prior to surgery (immediately after the patient was intubated) which was about 2-2.5 hours prior to Phase 1 so that the entire tissue area was pre-cooled. The ECB placed in the rectum effectively cooled the rectum, pelvic nerves, urethra, bladder, and prostate without obstructing the surgical field.

Assessment of Continence

Post-operative continence was assessed by means of addressed and stamped landmark postcards (given to patients at their pre-operative appointment). Patients were instructed to return the postcards as they achieved the corresponding landmark (e.g. landmark 1: One pad/day; landmark 2: Pad free). Continence was defined as the use of zero pads (pad free). Return to continence is a measurement of recovery of nerve function and is also a surrogate for the more difficult to measure return to sexual potency. A procedure that limits nerve damage as measured by rapid return to continence should also reduce loss of sexual functioning and decrease the time needed for return of potency.

Data were analyzed using SAS software (SAS, Cary, N.C.) with statistical significance considered to be p<0.05. Baseline characteristics between groups were analyzed with two-group two-tailed t-tests. The primary clinical outcome was time to zero urinary pads. The Kaplan-Meier method was utilized to compare the time to zero pads; the log-rank statistic was used to test for significant differences. Cox proportional hazards regression was used to compare continence between groups after adjusting for baseline characteristics including age, AUAss, IIEF-5, BMI, prostate weight, nerve-sparing, clinical stage and learning curve all of which might affect return to continence.

At no point was there significant deviation (>1° C.) from standard core body temperature in any of the patients. Intracorporeal temperatures were assessed with the ECB alone and with cold intracorporeal irrigation (4° C.). With ECB alone, the median T was 28.30° C. (range: 17.5-35.4° C., SD 3.54, Cl 1.04). When adjunctive cold irrigation was used, the median T dropped to 25.10° C. (range: 18.0-30.0, SD 2.93, Cl 0.86), (p<0.0001). The median nadir temperature achieved was 21.0° C. (range: 15.0-29.3° C., SD 3.29, Cl 0.97).

Locoregional hypothermia added minimal operative time. Estimated blood loss in the hypothermia group was 86.5 cc (range: 50 cc-150 cc) and was not significantly different compared to the control group. Of 50 patients, there was one complication unrelated to cooling requiring ICU admission for 24 hour observation due to an anti-emetic extra-pyramidal side effect. There were no complaints of rectal discomfort or damage.

Since the initial cohort of patients described above, an additional 70 patients have undergone hypothermic prostatectomy. Cooling has been continued in a subset of these patients for one hour in the recovery room for extended cooling. Intrarectal and intracorporeal temperatures have been reduced further (to 10-15° C.) by more effective cooling. Post-surgery cooling for 4-6 hours to further reduce inflammation is undergoing evaluation.

Figure 2:
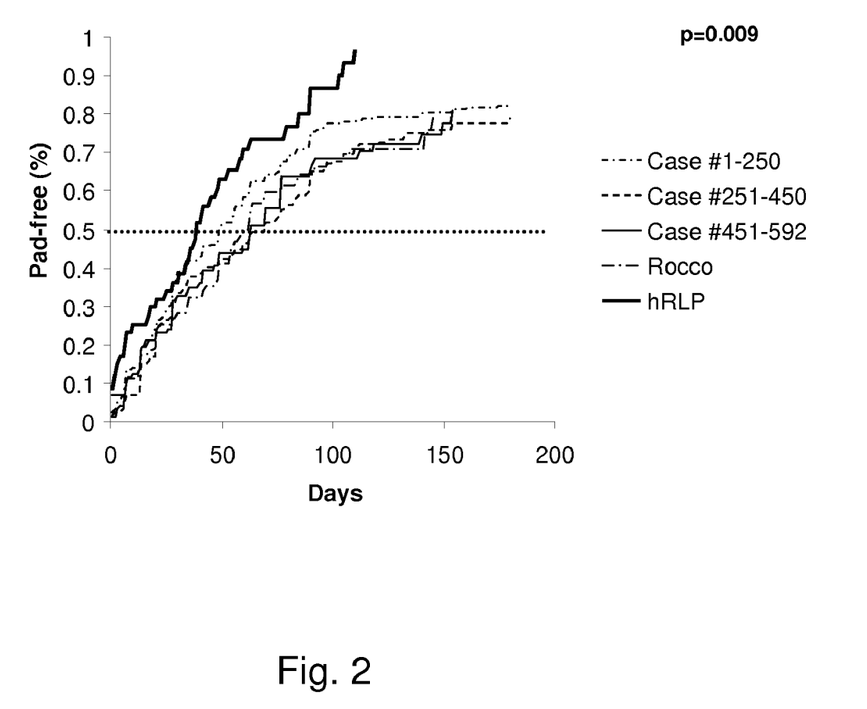
FIG. 2 is a graph demonstrating that the results were not affected by the experience of the surgeon (learning curve).

To maximize statistical power time to no-pads was analyzed in the hRLP group compared to the entire operative group demonstrating a highly statistically significant benefit to cooling. To account for differences in baseline characteristics, multivariate Cox proportional hazards regression was used to demonstrate a faster return to continence for the hRLP group (HR=1.66, p=0.014). Next, surgical experience (i.e. learning curve) was evaluated by comparing subgroups over the entire cohort of 667 patients (i.e. case #1-250, #251-450 etc). Univariate and multivariate analysis demonstrated no evidence of improved continence with experience (FIG. 2); the hRLP group, however, showed faster return of continence in both univariate and multivariate analysis compared to other subgroups.

Figure 3:
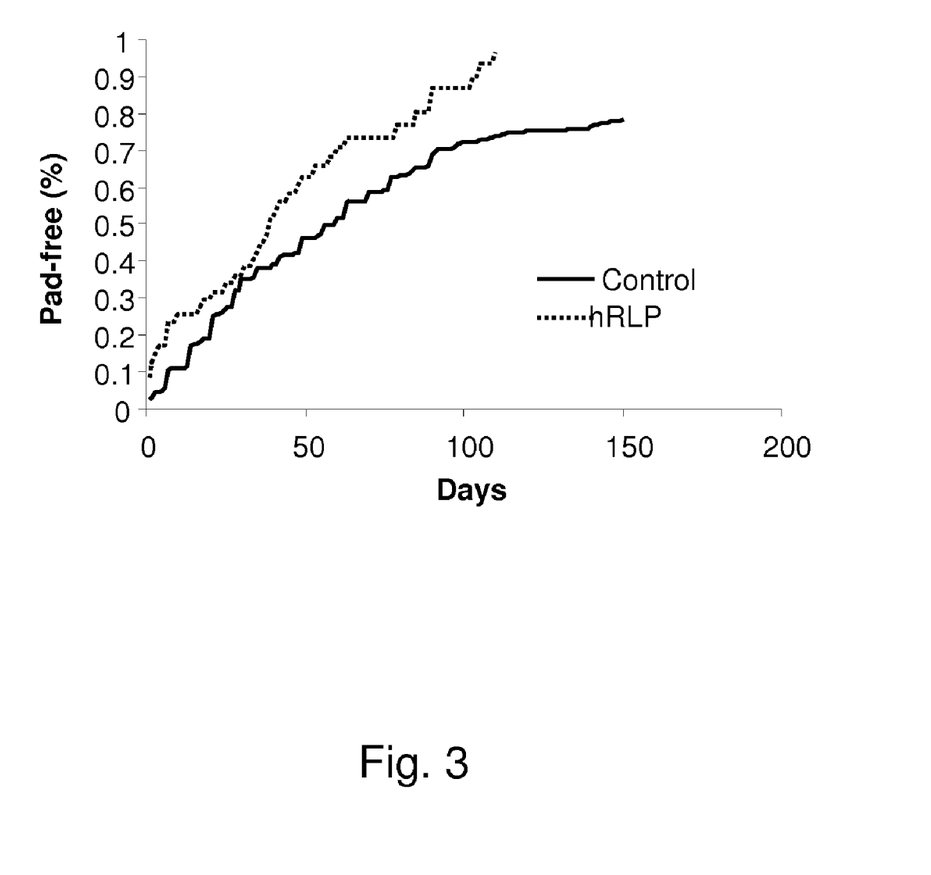
FIG. 3 is a graph illustrating return to urinary continence due to a method of the invention.

The continence data were obtained by validated self administered questionnaires thereby limiting physician related bias. As discussed, controls for the analysis were extensively evaluated for learning curve, technique, and baseline characteristics. Whether or not long term continence rates will be affected by deeper or longer lasting hypothermia awaits longer follow-up. Time to zero-pad status was determined in 47/47 patients in the hRLP group (100%) and 590 of 667 controls (88%). FIG. 3 demonstrates Kaplan-Meier analysis of time to zero pads. Return to continence was significantly faster for the hypothermia group (median=39 days) compared to the entire control group (median=59 days, p=0.002, log-rank test), representing a 33.9% improvement in time to continence. At 3 months 86.8±5.8% of the hRLP group versus 68.6±2.0% of the control group were pad-free.

Figure 4:
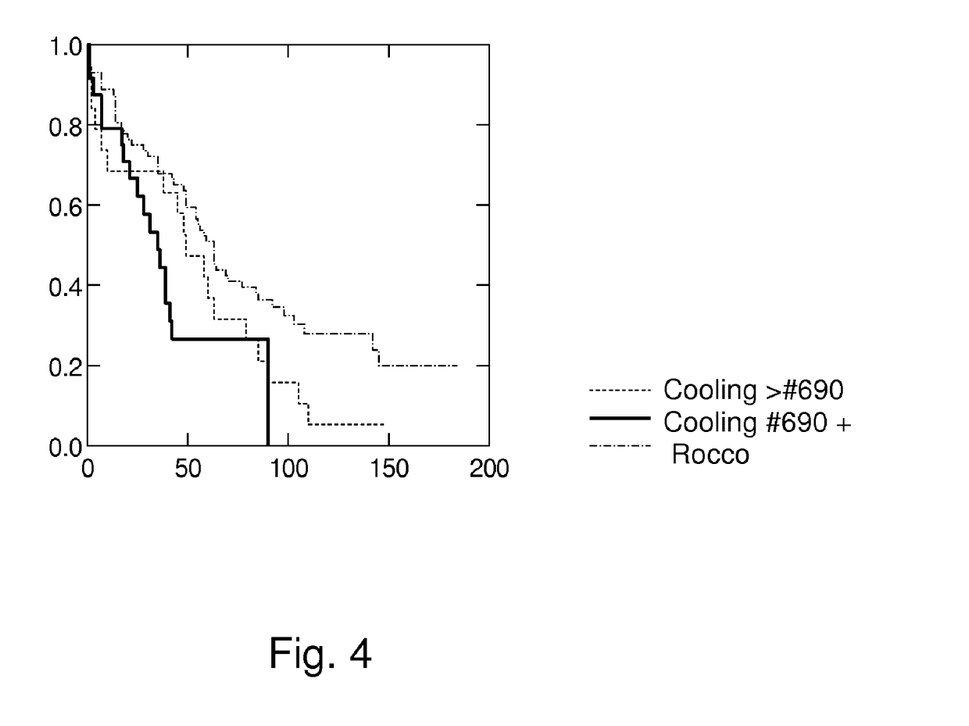
FIG. 4 is a survivor plot comparing return of continence with different cooling regimes to the Rocco method without cooling.

FIG. 4 shows a Survivor plot analysis (the MANTEL method with a Chi-Square statistic of 8.596 with two degrees of freedom and a significance level (p value) of 0.014) comparing Rocco method patients with no cooling to patients with two slightly different cooling regimes. As explained above, the initiation of cooling was changed to an earlier time for patient #690 and above. As the plot illustrates, the earlier and longer cooling resulted in more rapid return to continence. Presumably the longer cooling regime allowed critical tissues to reach a lower temperature and/or allowed effective cooling of a larger volume of tissue. This suggests the utility of longer and/or more extreme hypothermia.

In univariate analyses including all patients, median time to zero pads increased significantly with older age, higher AUAss, increasing prostate weight and decreasing IIEF-5 and (00.01 for each, see Table 2). BMI, clinical stage and nerve-sparing were not associated with return to continence in Kaplan-Meier analyses.

TABLE 2

Kaplan-Meier Univariate Analysis for Time to Zero Pads

| Variable | Category | Median time to 0 pads | Log-Rank test p-value |
| --- | --- | --- | --- |
| Age | ≤56 | 31 | <0.001 |
|  | 57-61 | 60 |  |
|  | 61-68 | 58 |  |
|  | >68 | 77 |  |

TABLE 2-continued

Kaplan-Meier Univariate Analysis for Time to Zero Pads

| Variable | Category | Median time to 0 pads | Log-Rank test p-value |
| --- | --- | --- | --- |
| AUAss | ≤3 | 48 | 0.001 |
|  | 4-7 | 58 |  |
|  | 8-12 | 49 |  |
|  | >12 | 63 |  |
| IIEF-5 | ≤17 | 89 | <0.001 |
|  | 18-22 | 60 |  |
|  | 22-24 | 40 |  |
|  | 25 | 35 |  |
| Prostate Weight | ≤39 | 47 | 0.011 |
|  | 39.1-47.6 | 63 |  |
|  | 47.7-59.3 | 49 |  |
|  | >59 | 60 |  |
| BMI | ≤24.4 | 56 | 0.233 |
|  | 24.5-26.5 | 51 |  |
|  | 26.6-28.8 | 49 |  |
|  | >28.8 | 59 |  |
| Nerve-sparing | No | 49 | 0.508 |
|  | Yes | 56 |  |
| Clinical Stage | I | 55 | 0.727 |
|  | II | 60 |  |
|  | III | 35 |  |
| Learning Curve | #1-250 | 49 | 0.009 |
|  | #251-450 | 64 |  |
|  | #451-592 | 63 |  |
|  | #593-667 | 59 |  |
|  | #668-717 | 39 |  |
| Rocco Stitch | No (#1-592) | 56 | 0.195 |
|  | Yes (#593-717) | 49 |  |
| hRLP | No (#1-667) | 59 | 0.002 |
|  | Yes (#668-717) | 39 |  |

To address potential differences between groups in baseline characteristics and to adjust for independent effects of covariates on time to continence, multivariate analysis utilizing Cox proportional hazards regression was performed on bladder neck sparing technique and clinical disease stage (see Table 3). Age, AUAss, IIEF-5 and BMI were significant independent predictors of time to continence. However, nerve-sparing was not a significant predictor. After adjusting for all potential co-variables, the hazard ratio for hRLP was 1.66 (95% CI: 1.11-2.49, p=0.014) indicating faster return to continence in the hRLP group relative to the control group.

TABLE 3

Cox Regression Multivariariate Analysis of Covariates

| Variable | Coefficient | Hazard Ratio | 95% Confidence Interval Lower | 95% Confidence Interval Upper | p-value |
| --- | --- | --- | --- | --- | --- |
| Age | −0.0253 | 0.9750 | 0.9614 | 0.9888 | <0.001 |
| AUAss | −0.0148 | 0.9853 | 0.9711 | 0.9997 | 0.046 |
| IIEF-5 | 0.0216 | 1.0218 | 1.0057 | 1.0383 | 0.008 |
| BMI | −0.0373 | 0.9634 | 0.9380 | 0.9895 | 0.006 |
| Nerve-Sparing | −0.1236 | 0.8837 | 0.7316 | 1.0675 | 0.200 |
| Stage (I vs II vs III) | −0.0587 | 0.9430 | 0.7770 | 1.1445 | 0.553 |
| Prostate Weight | −0.0029 | 0.9917 | 0.9922 | 1.0021 | 0.256 |
| Learning Curve | −0.0004 | 0.9996 | 0.9990 | 1.0001 | 0.116 |
| hRLP (No vs Yes) | 0.5081 | 1.6621 | 1.1096 | 2.4898 | 0.014 |

To assess the potential impact of learning curve time to zero pads for different subgroups of consecutive patients over time was compared using Kaplan-Meier analysis (Table 2 and FIG. 3) and Cox regression. Although time to continence differed significantly between consecutive subgroups in univariate analysis (p=0.009, log rank test), there was no consistent trend in median time to zero pads across groups to suggest a learning effect. Furthermore, in multivariate analysis, there was no evidence of improved continence with experience when learning curve was measured as a continuous variable by consecutive patient number. The hazard ratio for learning curve after adjusting for other factors was HR=0.9996 (95% CI: 0.999-1.000, p=0.116).

The posterior urethral plate reconstruction/posterior stabilization stitch (Rocco technique [Rocco et al. (2006) J. Urol. 175:2201-6]) was recently introduced into the surgical method and used on the most recent control subgroup (#593-667). Adjusting for differences in baseline characteristics for both groups utilizing multivariate Cox regression analysis, the hypothermic group achieved a faster pad-free status relative to the Rocco cohort (HR=1.7, 95% CI:1.009-2.918, p=0.046).

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. A method for enhancing recovery of biological function following surgery of the pelvis comprising the steps of:
   introducing a cooling balloon catheter into the rectum of a patient prior to surgery of the pelvis;
   inflating the cooling balloon catheter so that the balloon catheter engages the rectal wall and fills the rectal lumen;
   cooling the balloon catheter by introducing cooling fluid therein thus lowering the temperature of the balloon catheter and tissue in contact with the balloon catheter; and
   performing the surgery of the pelvis whereby hypothermia induced by the cooling balloon catheter enhances recovery of biological function wherein the biological function is urinary continence or sexual potency.

2. The method as claimed in claim 1 further comprising the step of continuing cooling with the balloon catheter after the surgery of the pelvis is completed.

3. The method as claimed in claim 1, wherein the surgery of the pelvis is a surgical prostatectomy selected from the group consisting of open radical prostatectomy, robot assisted laparoscopic radical prostatectomy, laparoscopic radical prostatectomy and perineal prostatectomy.

4. The method as claimed in claim 1 further comprising a step of applying cooled aqueous liquid intracorporeally at the site of surgery.

5. The method as claimed in claim 1 further comprising a step of continuing cooling the balloon catheter when the patient is placed in the recovery room.

6. The method as claimed in claim 1, wherein the step of cooling begins as soon as the patient is intubated prior to initiation of surgery.

7. The method as claimed in claim 1, wherein the surgery of the pelvis is selected from group consisting of extravesical ureteral reimplantation, radical cystectomy and colorectal surgery.

8. A method for enhancing recovery of biological function following gynecological surgery of the pelvis comprising the steps of:
   introducing a cooling balloon catheter into the rectum of a patient prior to gynecological surgery;
   inflating the cooling balloon catheter so that the balloon catheter engages the rectal wall and fills the rectal lumen;
   cooling the balloon catheter by introducing cooling fluid therein thus lowering the temperature of the balloon catheter and tissue in contact with the balloon catheter; and
   performing the gynecological surgery whereby hypothermia induced by the cooling balloon catheter enhances recovery of biological function wherein the biological function is urinary continence.

9. The method as claimed in claim 8 further including the steps of introducing a cooling balloon catheter into the vagina of a patient prior to gynecological surgery, inflating the cooling balloon catheter so that the balloon catheter engages the vaginal wall filling the vaginal lumen and circulating cooling fluid through the cooling balloon catheter thereby cooling the vagina and adjacent tissues.

10. The method as claimed in claim 8, wherein the gynecologic surgery is selected from the group consisting of radical hysterectomy, pelvic organ prolapse repair, bladder surgery, open sacrocolpopexy, laparoscopic sacrocolpopexy and robot-assisted sacrocolpopexy.

11. A system for improving recovery urinary continence and/or sexual potency following surgery of the prostate comprising:
   a cooling balloon catheter insertable into the rectum of a patient;
   means for inflating the cooling balloon catheter so that the balloon catheter engages the rectal wall extending from the membranous urethra to the seminal vesicles; and
   means for cooling the balloon catheter thereby inducing hypothermia in the prostate and surrounding tissues, whereby recovery or urinary continence or sexual potency is improved.

12. The system of claim 11 further comprising means for applying cooled aqueous liquid intracorporeally at the site of surgery.

13. A method for enhancing recovery of biological function following prostate surgery comprising the steps of:
   introducing a cooling balloon catheter into the rectum of a patient prior to prostate surgery;
   inflating the cooling balloon catheter so that the balloon catheter engages the rectal wall extending from about the membranous urethra to about the seminal vesicles;
   cooling the balloon catheter by introducing cooling fluid therein thus lowering the temperature of the balloon catheter and tissue in contact with the balloon catheter; and
   performing the surgery of the prostate whereby hypothermia induced by the cooling balloon catheter enhances recovery of biological function wherein the biological function is urinary continence or sexual potency.

14. The method as claimed in claim 13 further comprising a step of applying cooled aqueous liquid intracorporeally at the site of prostate surgery.

15. A method for enhancing recovery of biological function following a surgery of the pelvis comprising the steps of:

introducing a cooling balloon catheter into the rectum of a patient prior to a surgery of the pelvis;

inflating the cooling balloon catheter so that the balloon catheter engages the rectal wall and fills the rectal lumen;

cooling the balloon catheter by introducing cooling fluid therein thus lowering the temperature of the balloon catheter and tissue in contact with the balloon catheter;

applying cooled aqueous liquid intracorporeally at the site of the surgery; and performing the surgery of the pelvis whereby hypothermia induced by the cooling balloon catheter reduces tissue damage and enhances recovery of biological function wherein the biological function is urinary continence or sexual potency.

16. A system for improving recovery urinary continence and/or sexual potency following a surgery of the prostate comprising:

a cooling balloon catheter insertable into the rectum of a patient;

means for inflating the cooling balloon catheter so that the balloon catheter engages the rectal wall extending from the membranous urethra to the seminal vesicles;

means for cooling the balloon catheter thereby inducing hypothermia in the prostate and surrounding tissues; and means for applying cooled aqueous liquid intracorporeally at the site of the surgery.

17. A method for enhancing recovery of biological function following a prostate surgery comprising the steps of:

introducing a cooling balloon catheter into the rectum of a patient prior to a prostate surgery;

inflating the cooling balloon catheter so that the balloon catheter engages the rectal wall extending from about the membranous urethra to about the seminal vesicles;

cooling the balloon catheter by introducing cooling fluid therein thus lowering the temperature of the balloon catheter and tissue in contact with the balloon catheter;

applying cooled aqueous liquid intracorporeally; and performing the surgery of the prostate whereby hypothermia induced by the cooling balloon catheter reduces tissue damage and enhances recovery of biological function wherein the biological function is urinary continence or sexual potency.

18. A method for enhancing recovery of biological function following gynecological surgery of the pelvis comprising the steps of:

introducing a cooling balloon catheter into the rectum of a patient prior to gynecological surgery;

inflating the cooling balloon catheter so that the balloon catheter engages the rectal wall and fills the rectal lumen;

cooling the balloon catheter by introducing cooling fluid therein thus lowering the temperature of the balloon catheter and tissue in contact with the balloon catheter;

introducing a second cooling balloon catheter into the vagina of a patient;

inflating the second cooling balloon catheter so that the second balloon catheter engages the vaginal wall filling the vaginal lumen;

circulating cooling fluid through the second cooling balloon catheter thereby cooling the vagina and adjacent tissues; and performing the gynecological surgery whereby hypothermia induced by the cooling balloon catheter reduces tissue damage and enhances recovery of biological function wherein the biological function is urinary continence.

* * * * *